Figure 1A:
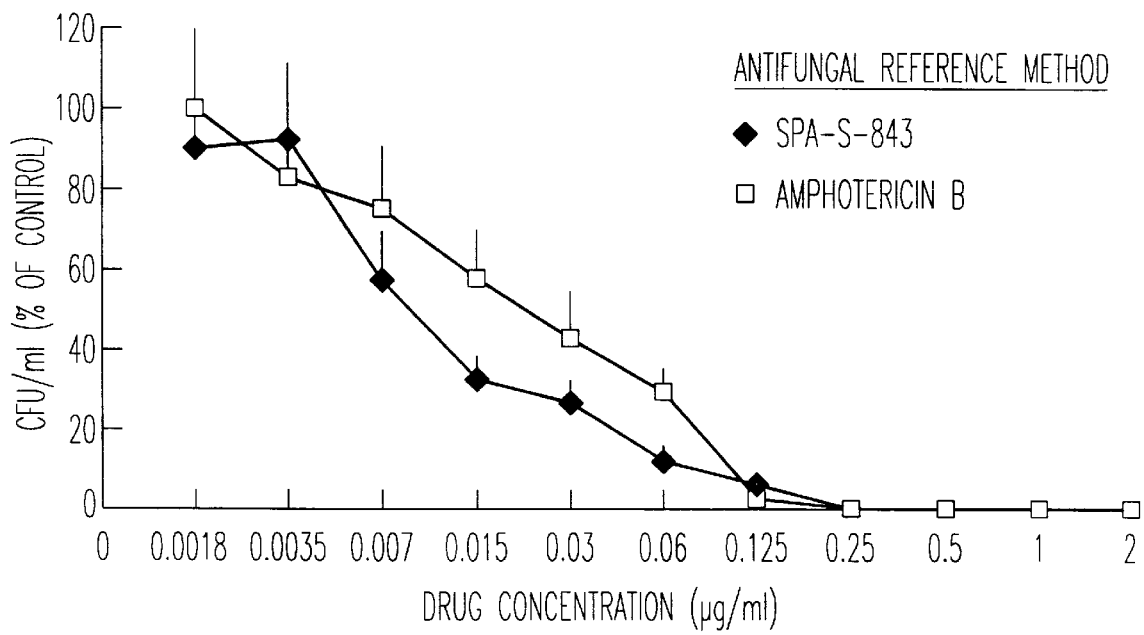

United States Patent [19]
Bruzzese

[11] Patent Number: 5,908,834
[45] Date of Patent: Jun. 1, 1999

[54] PARTRICIN DERIVATIVES IN THE PROPHYLACTIC AND/OR CURATIVE TREATMENT OF FUNGAL CONTAMINATION OF CELL CULTURES AND OF TISSUES

[75] Inventor: Tiberio Bruzzese, Milan, Italy

[73] Assignee: Prospa B.V., Hoofddorp, Netherlands

[21] Appl. No.: 08/950,142

[22] Filed: Oct. 14, 1997

[30] Foreign Application Priority Data

Sep. 16, 1997 [IT] Italy .................................. MI97A2096

[51] Int. Cl.⁶ .................................................... A61K 31/70
[52] U.S. Cl. .............................................................. 514/31
[58] Field of Search ................................................. 514/31

[56] References Cited

U.S. PATENT DOCUMENTS

| 3,780,173 | 12/1973 | Bruzzese et al. | 514/31 |
|---|---|---|---|
| 3,961,047 | 6/1976 | Bruzzese et al. | 514/31 |
| 5,296,597 | 3/1994 | Bruzzese et al. | 544/106 |
| 5,298,495 | 3/1994 | Bruzzese et al. | 514/31 |

OTHER PUBLICATIONS

*Samson Wright's Applied Physiology*, Eleventh Ed., C.A. Keele, Ed., Oxford Univ. Press, London, p. 64, 1965.

P.B. Weisz, *The Science of Biology*, McGraw–Hill, New York, pp. 439–440, 1959.

T. Bruzzese et al, *Eur. J. Med. Chem.*, vol. 31, pp. 965 and 972 (1996).

*Primary Examiner*—Raymond Henley, III
*Attorney, Agent, or Firm*—Oblon, Spivak, McClelland, Maier & Neustadt, P.C.

[57] ABSTRACT

The use of ester and/or amide derivatives of partricin A and/or B to inhibit or forestall the growth of yeasts and molds in cell cultures of animal or vegetable origin, including hybridomas and cells whose DNA was modified. This use consists in adding the afore-said derivatives to the cell cultures in concentrations such as to inhibit the growth of yeast and molds but such as not to be toxic for the cell cultures themselves. The invention can be made use of, for instance, in the production of vaccines and in the conservation of organs and tissues intended for transplantation.

26 Claims, 4 Drawing Sheets

PARTRICIN DERIVATIVES IN THE PROPHYLACTIC AND/OR CURATIVE TREATMENT OF FUNGAL CONTAMINATION OF CELL CULTURES AND OF TISSUES

Cell culture is a technique well known to the experts in the art, through which eukaryote cells are allowed to grow and multiply in both monolayer cultures and industrial cultures according to procedures f.e. similar to those through which prokaryote cells are fermented to produce i.e., substances of the antibiotic type.

The eukaryote cells in question are from different sources, that is, originating from man, from various animal species (mouse, rabbit etc.) and also from the vegetable world and from various apparatuses or organs thereof.

A good example of cell collection is The American Type Culture Collection (ATCC); other examples of cell collections can be found among the institutions accepted as international deposits according to the Budapest treaty.

A large number of highly valuable cell cultures are frequently used for various purposes ranging from scientific research to a variety of therapeutic scopes.

It is well known to the experts in the field that these cell cultures are frequently subject to contamination by bacterial or fungal agents, for which reason they must be protected with the use of suitable antibiotic or chemotherapeutic substances or else—for their intrinsically dangerous nature and rapidly growing microbial charge—will have to be disposed of, with consequent serious, even economical, loss.

It is also known that the antifungal agent more commonly used from a clinical-therapeutic point of view, but also in cell cultures, is amphotericin B, as such or in the form of a water-soluble sodium deoxycholate complex, or other forms.

Amphotericin B, like other substances of the polyene antibiotic class, acts on the mycetes (yeasts and moulds) with a mechanism connected with its affinity (binding) for the membrane sterols in fungine cell; its mechanism of action is explained as a mechanism leading to alteration of cell permeability with consequent intracellular potassium loss and loss of other essential metabolites. Since also the mammalian cell membranes contain sterols, they too can be a target for the polyenes, with cytotoxic consequences.

For the foregoing reasons amphotericin B proves very toxic in vitro, as also occurs in vivo at a clinical level, for cell structures (cytotoxicity), leading frequently to culture growth inhibition and death of the cell itself.

We have now found—being it the subject of the present patent application—that several derivatives (U.S. Pat. No. 5,296,597, U.S. Pat. No. 5,298,495, U.S. Pat. No. 3,780,173 and U.S. Pat. No. 3,961,047) of the polyene partricin (The Merck Index 12a Edition, no. 7181) as well as each of its constituents A and B, specially of partricin A, have a strong antifungal activity in vitro and in vivo, generally higher than that of amphotericin B; furthermore, the cytotoxicity of these derivatives is lower (higher selectivity of action towards fungine cell membrane than towards eukaryote cell membrane) and they can therefore be more profitably used to protect a large variety of cell and tissue cultures in vitro or ex vivo from contamination by mycetes, fungi and yeasts.

The water solubility of some of the above mentioned partricin derivatives is an additional advantage in their use.

The partricin A and/or partricin B derivatives that we have used are those described in the above mentioned U.S. Patents, made up in practice, of esters and amides on the carboxyl group at C-18 of the macrolide ring, optionally substituted on the amino group of the mycosamine radical with an acyl group and their salts with organic and inorganic acids acceptable in the pharmacological and pharmaceutical practice.

In particular, the amide derivatives of partricin A and/or B described in U.S. Pat. No. 5,296,597 are secondary or tertiary amides of the carboxyl group at C-18 of the macrolide ring. In partricin A and/or B derivatives described in U.S. Pat. No. 5,298,495 the carboxyl group at C-18 of the macrolide group forms an alkyl ($C_1$–$C_6$) ester or an amide, neutral or containing an additional basic nitrogen containing function, and the primary amino group of the mycosamine portion forms an amide bond with the carboxyl group of an aliphatic acid of 2–4 carbon atoms containing an additional basic nitrogen containing group.

Other derivatives of partricin suitable for the use and methods of this invention are the alkyl esters of partricin, e.g. $C_1$–$C_4$ alkyl esters, in particular the methyl ester of partricin complex (mepartricin) and of partricin A and/or B described in U.S. Pat. No. 3,780,173 and U.S. Pat. No. 3,961,047.

The description and examples of U.S. Pat. Nos. 5,296,597, 5,298,495, 3,780,173 and 3,961,047 concerning the preparation of partricin A and/or B derivatives mentioned above, are incorporated by reference in the present application.

The scope of this invention includes the use of those derivatives of partricin A and/or B having the usual configuration of partricin as well as those derivatives of partricin A and/or B having "all trans" configuration which can be obtained, for instance, by UV or sun light exposure (Bruzzese T. et al, Il Farmaco Ed. Sci. 4, 331–334, 1974).

The substance that we have more thoroughly studied for the purpose of the use and methods of the present invention, is N-dimethylaminoacetyl-partricin A 2-dimethylaminoethylamide diascorbate (identification code: SPA-S-843); the tests were conducted in comparison with amphotericin B.

The two substances were dissolved in bidistilled sterile water at the concentration of 2000 $\mu$g/ml. Dilutions were performed in McCoy medium supplemented with penicillin-streptomycin (100 U/ml+100 $\mu$g/ml) as antibacterial agents, up to concentrations of 200-100-50-25-12.5-6.25-3.12-1.56 $\mu$g/ml.

Of the several cell lines used, the ones exemplified here—without any limiting intent and purpose—to study the toxic effects of SPA-S-843 and of amphotericin B on cell vitality and proliferation capacity, were well defined murine cell lines: L1210 (leukemic B cells) and SR-4987 (stromal cells), and myeloid precursors in freshly isolated murine bone marrow cells (mu-BMC). The cell lines were maintained through subculture in plastic bottles containing 25 $cm^2$ McCoy medium (Seromed—Germany) supplemented with 5% FCS (Gibco, USA). The mu-BMC cells were obtained from murine femurs and tibias of DBF 1 female mice, as already described (Pessina A. et al.—"Stimulating factor produced by murine adrenocortical tumor cells"—J. Natl. Cancer Inst., 76, 1095–9, 1986).

The study comprised:
A) Confirmation of the in vitro antifungal activity of SPA-S-843 compared to that of amphotericin B against *Candida albicans*, using a reference method and a microtiter test (MTT).
B) Evaluation of the toxicity of the two polyenes on different well-defined cell lines (L1210 and SR-4987) and on hematopoietic precursors (GM-CFU) in order to calculate an in vitro therapeutic and activity index with a view to using SPA-S-843 as a antifungal agent in cell cultures.

C) In tests of cell contamination by mycetes and to verify the curative effect in cell cultures and transplantation tissues.

A) Antifungal Activity

We used a *Candida albicans* clinical isolate (Type I, serotype 2576174) maintained by subculture on Sabouraud Dextrose Agar slant. The test was conducted in liquid suspension followed by plating in Sabouraud Dextrose Agar (SDA, Difco USA) according to Galgani et al. (Reference method for broth dilution antifungal susceptibility testing of yeasts; Proposed standard. The National Committee for Clinical Laboratory Standards (NCCLS) 12, 1–22, 1995).

In brief, 5 colonies, 1-mm in diameter, from a *C. albicans agar* culture were suspended in 5 ml of McCoy basic medium and shaken for 30 minutes. 100 µl from the resulting suspension were diluted in 5 ml of McCoy medium and incubated at 35° C. for 24 hours, obtaining a yeast suspension of about $1-2 \times 10^7$ CFU (CFU/ml). Working suspensions were prepared with dilutions of 1:100, 1:1000 and 1:10.000 in McCoy medium obtaining $1-2 \times 10^5$, $1-2 \times 10^4$ and $1-2 \times 10^3$ CFU/ml as ascertained by counting the colonies in Sabouraud Dextrose Agar.

To test the antifungal activity, 0.1 ml from each drug concentration was put in $13 \times 100$ mm plastic test tubes. The control test tubes contained 0.1 ml of diluent without antifungal agent. Each test tube was inoculated with 0.9 ml of *C. albicans* suspension and stirred. After 48-h incubation at 37° C. the number of vital yeasts at the different drug concentrations was determined by counting the CFU on Agar Dextrose Sabouraud.

The antifungal activity was also tested by a short term MTT test as follows, for mammalian cells: 50 µl of a 1:2 dilution of SPA-S-843 and amphotericin B were placed in each well and added with 50 µl of *C. albicans* suspension ($10^7$ cells/ml). After 24-h incubation at 37° C. the Microtiter plates were examined by MTT as follows. The IC values were determined according to Reed and Muench (A simple method of estimating 50% end points—Am. J. Hyg., 27, 493, 1938).

B) Cytotoxicity by MTT Test

A microtiter test was used with 3-(4,5-dimethyl-2thiazolyl)-2,5-diphenyl-2-H-tetrazolium (MTT, Sigma, USA) according to Mossman et al. modified according to A.B. Kriegler et al.—J. Immunol. Methods, 103(1), 93–102 (1987).

In brief, 50 µl of a 1:2 serial dilution from 2 µg/ml to 0.015 µg/ml of each of the two drugs were placed in 96 wells of flat-bottom Microtiter plates then each well was added with a 50 µl cell suspension ($6 \times 10^3$ cells/ml). The cultures were incubated for 7 days at 37° C. in air+5% $CO_2$ and finally 20 µl of MTT at a conc. of 5 mg/ml in PBS were added to each well. After 3-h incubation at 37° C. the cultures were destroyed with 100 µl of a lytic buffer prepared with sodium dodecylsulfate/dimethylformamide/acetic acid/HCl. After further overnight incubation, the optical density (OD) at 620 nm was determined with a microplate LP200 detector. The O.D. of the wells with no cells was considered as 0% proliferation. The O.D. of the wells with growing cells in drug-free medium was considered as 100% proliferation. The drug cytotoxicity was calculated as the minimum concentration leading to 50% inhibition of cell growth in vitro ($IC_{50}$).

Cytotoxicity by Clonogenicity Test in Agar

The clonogenic capacity of L1210 cells was tested by culturing 300 cells in 0.9 ml of complete enriched medium (McCoy+10% FCS, 10 mM sodium pyruvate, 4% NEAA (100×), 4% Mem Vit (100×)+0.3% agar in 35 mm Petri plates.

SPA-S-843 and amphotericin B (100 µl) had previously been added to the Petri plates at serial concentrations of from 25 to 0.19 µg/ml. The control plates contained 100 µl of culture medium. The colonies were counted after 7 days of incubation at 37° C. in an atmosphere of air+5% $CO_2$. Proliferation of precursors of murine granulocyte macrophages (GM-CFU) was assessed in a soft agar culture system according to Robinson et al. (Stimulation by normal and leukemic mouse sera of colony formation in vitro by bone marrow cells—J. Cell Physiol., 69, 83–92, 1967).

In brief, $10^5$ murine, vital, mononucleate bone marrow cells (BMC) were cultured in 0.9 ml of McCoy enriched medium—0.33% agar (Seromed, Germany) containing 20% FCS+2% of cell culture-conditioned medium. 100 µl of a suitable concentration of each drug had been previously added to each culture plate. The colonies (>50 cells) were counted using an inverted light microscope after 7 days of incubation at 37° C.

C) Experimental Contamination of Cell Cultures 2 ml of L1210 and SR-4987 cell suspensions ($10^4$ cells/ml) were plated in triplicate in 24-well plates. After 24-h growth, each culture was added with 100 µl of SPA-S-843 or amphotericin B up to a final concentration of 1 µg/ml. The control wells did not contain the drugs. The cultures were kept under microscope observation after 12-24-48 and 72 hours of incubation at 37° C. and the yeast colonies counted. At 96 hours a subculture of each cell line was performed in the drug absence and, after one week, the cell supernatant was controlled to ascertain the presence of yeasts.

Data Elaboration and Statistical Analysis

The data were elaborated in order to obtain information about in vitro activity and therapeutic efficacy of the drugs.

The following arbitrary parameters were calculated:

Activity index (A.I.)=$IC_{50}$ cells/$IC_{50}$ yeast

Therapeutic index (T.I.)=$IC_{10}$ cells/$IC_{90}$ yeast

The dose/response relationship was studied through linear regression and calculation of the correlation coefficient (r).

Statistical differences between mean values were evaluated with Student's t test and considered significant at p<0.05

SPA-S-843 and Amphotericin B Antifungal Activity

Figure 1B:
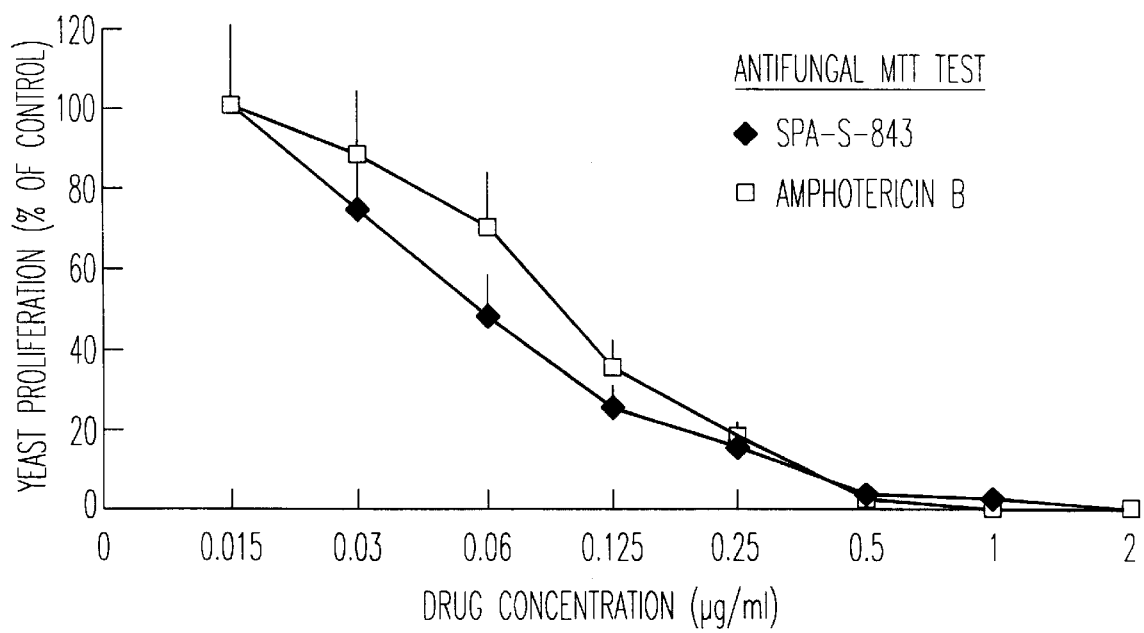

It was assessed in Sabouraud Agar (FIG. 1A) and through the microtiter test (MTT) (FIG. 1B).

The diagrams show that the antifungal activity is dose-related and the linearity test gives an identical correlation coefficient.

Figure 2A:
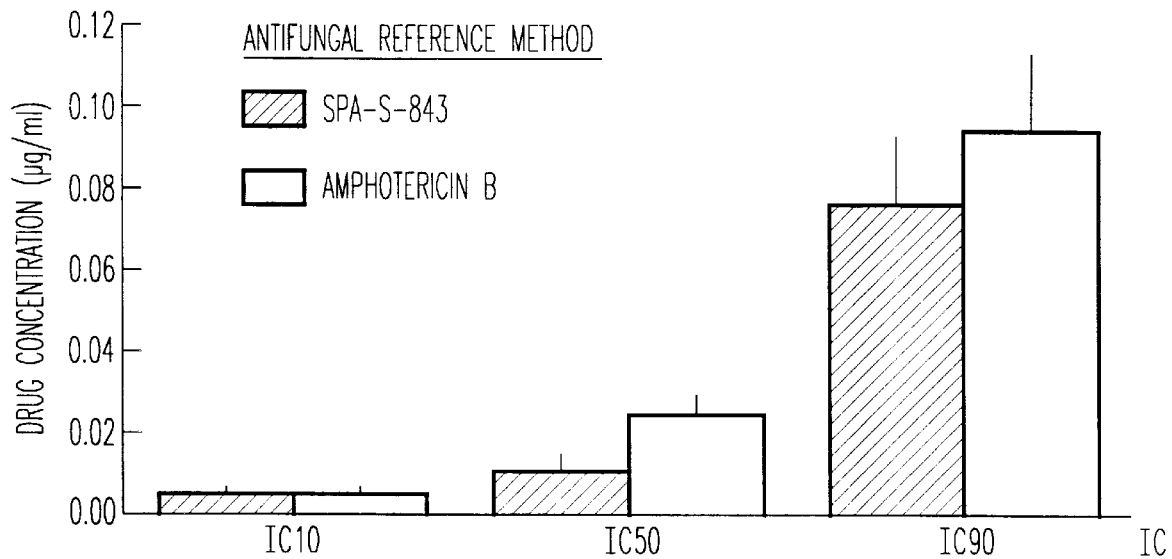
Figure 2B:
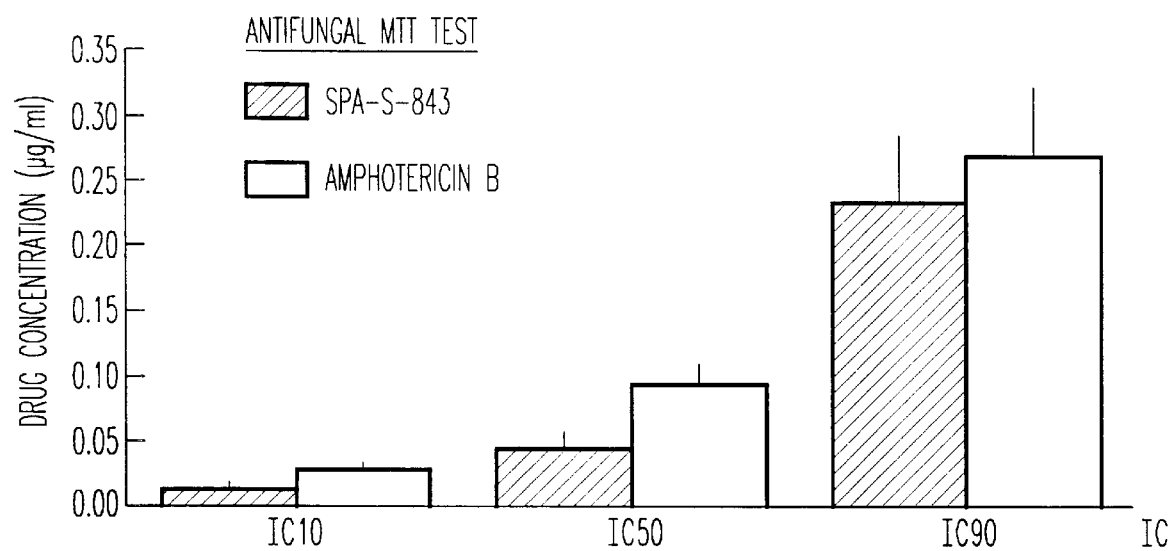

The antifungal activity tested with the MTT method demonstrates a dose-related kinetics, quite similar to that determined with the reference method; however, as shown in FIGS. 2A and 2B, the $IC_{10}$, $IC_{50}$ and $IC_{90}$ values calculated with the MTT test were 3 times higher which indicates that this test sensitivity is lower. Not withstanding this lower sensitivity the ratios between the $IC_{50}$ of SPA-S-843 and the $IC_{50}$ of amphotericin B were rather similar to those obtained with the reference method: in both cases however, SPAS-843 was twice more active than amphotericin B in both tests. This will enable the use of lower concentrations of SPA-S-843 in cell cultures, with reduced cytotoxicity for the cells involved.

SPA-S-843 and Amphotericin B Cytotoxic Effect on Proliferation of L1210 and SR-4987 Cells The results of drug cytotoxicity on cell proliferation, evaluated with the MTT test, are expressed as % of the O.D. values measured in the controls (untreated cells). The control O.D. values were 1081.9±106.5 for L1210 and 419.9±64.9 for SR-4987.

Figure 3A:
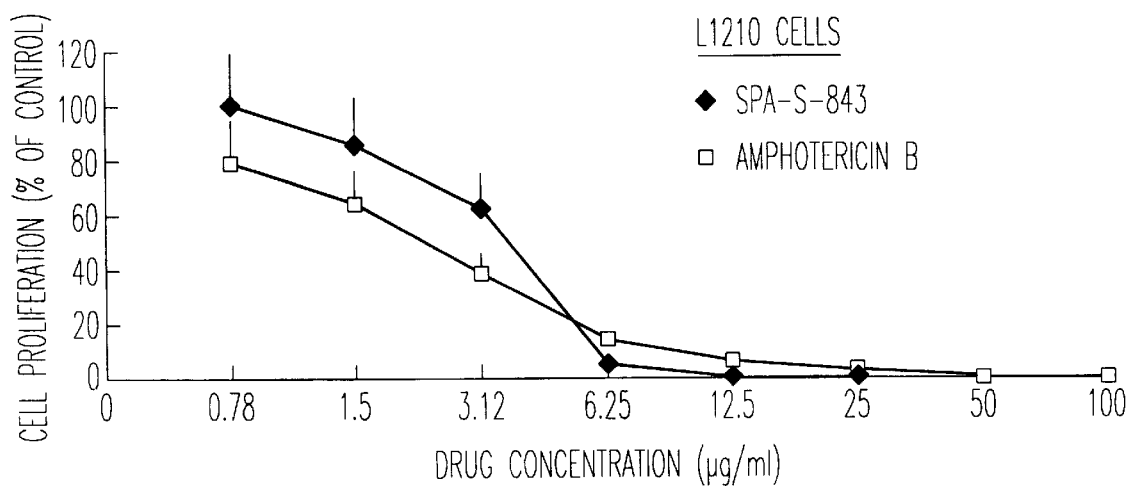
Figure 3B:
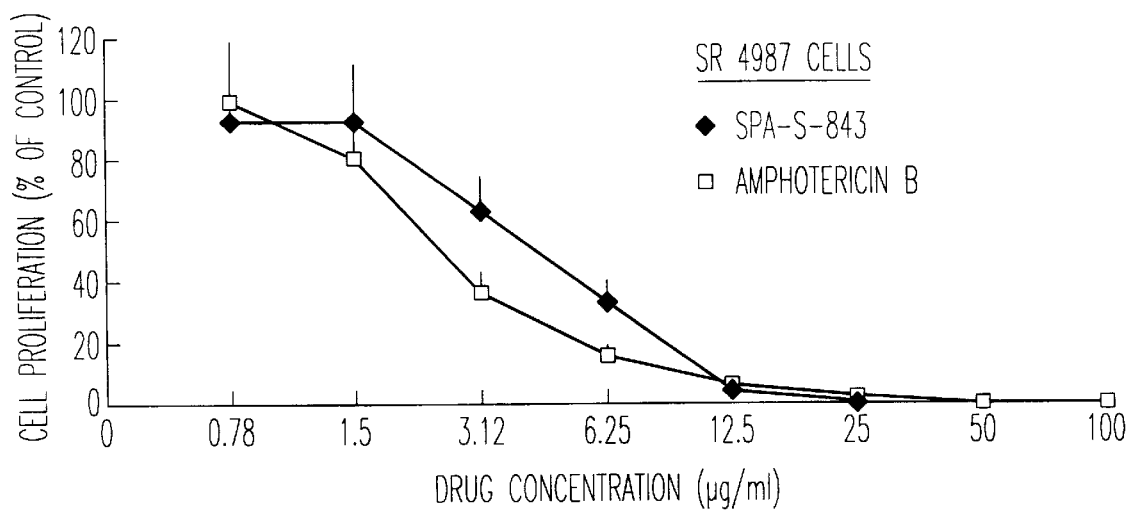

The diagrams in FIGS. 3A and 3B show the dose/response curves.

As confirmed by linear regression analysis, the toxic effect of SPA-S-843 and of amphotericin B shows a dose-related kinetics and the activity of the two drugs appears substantially similar.

Table 1 shows the $IC_{10}$ and $IC_{50}$ of the two drugs for each cell line. Examination of the differences between IC values confirms that the $IC_{10}$ and $IC_{50}$ of the two products do not significantly differ.

SPA-S-843 and Amphotericin B Cytotoxic Effect on Clonogenicity of L1210 and GM-CFU Cells.

The cytotoxicity of the two drugs on cell clonogenicity, evaluated through an agar test, were expressed as percent of the number of colonies counted in the controls (untreated cells).

The number of colonies in the controls was 153.3 in the case of L1210 and of 129.5±0.5 in the case of granulocyte macrophage precursors (GM-CFU).

Figure 4A:
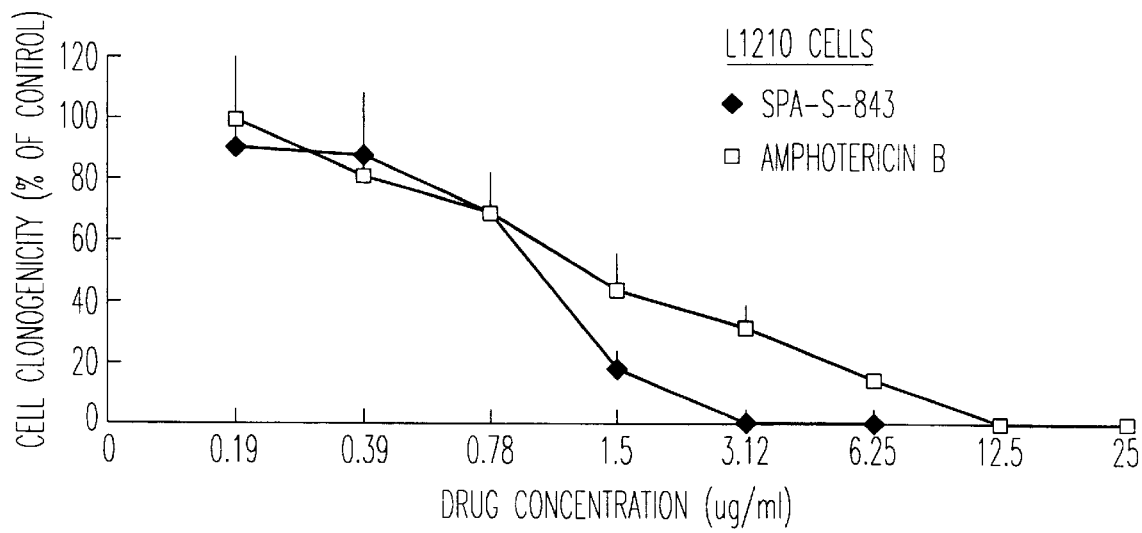
Figure 4B:
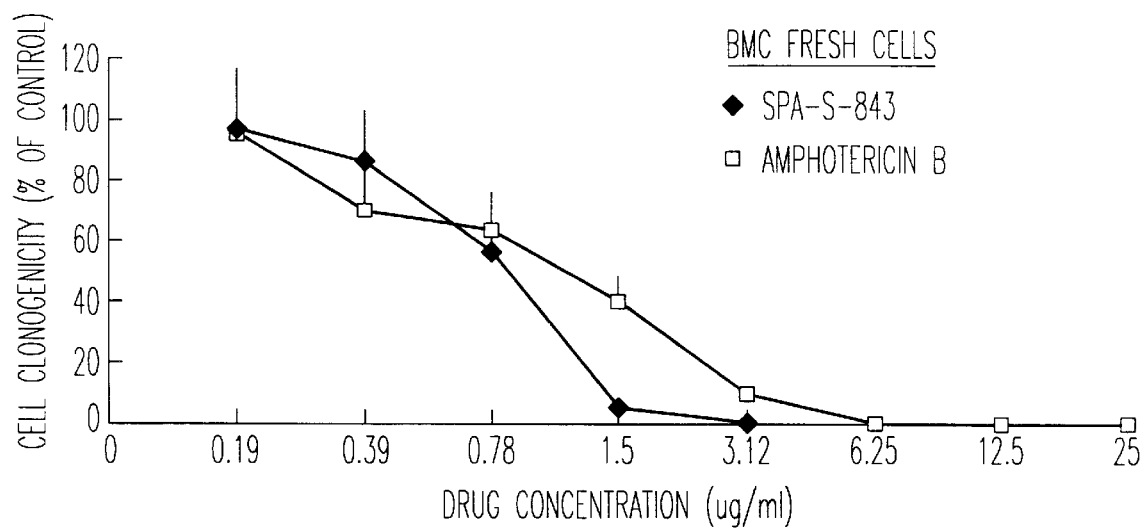

The diagrams in FIGS. 4A and 4B show the dose-response curves which appear similar for the two compounds as regards both L1210 and GM-CFU cells. Table 2 reports the $IC_{10}$ and $IC_{50}$ values for each cell line. In this case too the $IC_{10}$ and $IC_{50}$ of one product do not significantly differ from those of the other and their cytotoxicity is therefore comparable.

Parameter Comparison in vitro

The activity arbitrary indices in vitro were expressed as the relationship between $IC_{50}$ values determined on the cell lines and through antifungal activity tests. Table 3 regards the reference antifungal method and Table 4 regards the MTT antifungal test. Moreover the therapeutic index of both products for each cell line was calculated (Table 5).

As shown in Tables 3 and 4, no great difference was found in the results of the two antifungal tests and, at any rate, in some cell lines SPA-S-843 activity index was found better than that of amphotericin B, while in some other lines the contrary occurred: however, all in all, ratio R between SPA-S-843 activity indices and amphotericin B activity indices is often higher than 1, which demonstrates that, on the whole, SPA-S-843 activity index is higher than that of amphotericin B. Also the data in Table 5 show the SPAS-843 therapeutic arbitrary index is higher than that of amphotericin B.

Prevention of Experimental Contamination

This experiment represents a promising confirmation of SPA-S-843 concrete efficacy in cell cultures. As shown in Table 6, after 96 hours from *C. albicans* contamination ($10^2$ CFU/culture), no yeast growth was seen in SPA-S-843 pre-treated cultures, while amphotericin B activity was lower and occasionally failed to lead to complete sterilisation. The subcultures prepared at 96 hours were sterile during the 7 days of observation of the cultures treated with SPA-S-843. In the cell cultures prepared without drugs, a mean of 80–100 yeast colonies/culture were counted after experimental contamination.

Similar antifungal effects were observed during conservation of tissues intended for transplantation, infected with moulds and yeasts.

From the overall results reported above, the conclusion can be drawn that the typical exemplifying derivative of partricin A, SPA-S-843, tested against *C. albicans* through a reference method, exhibits very high activity, with a characteristic dose-related kinetics similar to that of amphotericin B. The $IC_{50}$ value of one substance differs to a significant extent, from that of the other. In fact, the ratio between the $IC_{50}$ of SPA-S-843 on yeasts and that of amphotericin B is 1:2, demonstrating a twice as high activity for SPA-S843. The same experimental design, repeated on *C. albicans* liquid cultures, by a microtiter (MTT) test, elicits a very similar dose-related response, though this method is 3-fold less sensitive than the reference method.

Tests to evaluate the in vitro cytotoxicity of the two products on animal cells were conducted on different, well established cell lines and on precursors of granulocyte macrophages (GM-CFU). The results show that the compounds differ in their toxicity and that this difference depends on the different sensitivity of the cell lines tested. If the data are regarded in their totality it appears that some arbitrary parameters, such as the activity and therapeutic indices, are higher for SPA-S-843.

Thanks to the fact that SPA-S-843 water solubility is higher, it can be better managed and more accurately diluted in culture media, which is an additional advantage in its use.

These results, along with studies on the capacity of SPA-S-843 to prevent fungine contamination, clearly suggest that this drug is to be considered the prototype of very useful molecules usable as prophylactic agents in the prevention of contamination, by yeasts and mould, of cell cultures, inclusive of those used in preparation of vaccines for human and veterinary use, and useful also for treating cell cultures already infected by yeasts, and in vitro organs intended for transplantation.

SPA-S-843 shares the above mentioned intended uses with the other above mentioned derivatives of partricin A and/or B. In particular, the cell cultures can be obtained from animal or vegetable cell lines or from hybridomas. The cells can come from any vegetable of animal species, including man, and derive from any tissue type. Such cells comprise tumor and staminal cells and cells with modified DNA.

Accordingly, one of the main objects of this inventon is the use of partricin A and/or B derivatives as antifungal agents against the contamination of cell cultures, in particular, an object of this invention is a method to prevent and/or cure contamination of cell cultures and of tissues in vitro or ex-vivo by fungal agents, consisting in the addition to cell cultures, sensitive to such fungal agents, of an ester or amide of partricin A and/or B at the carboxyl group bound at C-18 of the macrolide ring optionally substituted on the amino group of the mycosamine radical with an acyl group as described above in an amount (concentration) such as to be effective as an antifungal agent, but non toxic for the cell culture itself.

TABLE 1

$IC_{10}$ and $IC_{50}$ values of SPA-S-843 and of amphotericin B assessed in cell proliferation tests (mean values of 3 tests performed in triplicate)

|  | L1210 Cells | | SR4987 Cells | |
|---|---|---|---|---|
|  | $IC_{10}$ | $IC_{50}$ | $IC_{10}$ | $IC_{50}$ |
| SPA-S-843 (μg/ml) | 2.0 | 4.0 | 1.2 | 4.0 |
| Amphotericin B (μg/ml) | 1.0 | 2.5 | 1.2 | 2.6 |

TABLE 2

$IC_{10}$ and $IC_{50}$ values of SPA-S-843 and of amphotericin B assessed in cell clonogenicity tests (Mean values of 2 tests performed in duplicate)

|  | L1210 Cells | | BCM Cells | |
|---|---|---|---|---|
|  | $IC_{10}$ | $IC_{50}$ | $IC_{10}$ | $IC_{50}$ |
| SPA-S-843 (μg/ml) | 0.3 | 1.0 | 0.3 | 0.8 |
| Amphotericin B (μg/ml) | 0.4 | 1.3 | 0.2 | 1.2 |

TABLE 3

In vitro activity index (A.I.) of SPA-S-843 and amphotericin B pertaining to the reference antifungal method.

| | ACTIVITY INDEX | | | | | | | |
|---|---|---|---|---|---|---|---|---|
| | Proliferation | | | | Clonogenicity | | | |
| | L1210 | | SR-4987 | | L1210 | | BMC | |
| | $IC_{10}$ | $IC_{50}$ | $IC_{10}$ | $IC_{50}$ | $IC_{10}$ | $IC_{50}$ | $IC_{10}$ | $IC_{50}$ |
| SPA-S-843 | 324 | 207 | 229 | 319 | 32 | 73 | 50.5 | 56.6 |
| Amph. B | 166 | 162 | 264 | 110 | 59 | 57 | 5,6 | 54 |
| R | 1.95 | 1.27 | 0.86 | 2.9 | 0.54 | 1.28 | 9 | 1.04 |

R = A.I. SPA-S-843/A.I. Amphotericin B

TABLE 4

In vitro activity index (A.I.) of SPA-S-843 and of amphotericin B pertaining to the MTT antifungal test.

| | ACTIVITY INDEX | | | | | | | |
|---|---|---|---|---|---|---|---|---|
| | Proliferation | | | | Clonogenicity | | | |
| | L1210 | | SR-4987 | | L1210 | | BMC | |
| | $IC_{10}$ | $IC_{50}$ | $IC_{10}$ | $IC_{50}$ | $IC_{10}$ | $IC_{50}$ | $IC_{10}$ | $IC_{50}$ |
| SPA-S-843 | 97 | 51.8 | 69 | 79.8 | 9.7 | 18 | 15 | 14 |
| Amph. B | 27.7 | 43 | 44 | 29 | 9.8 | 15 | 7.5 | 14.3 |
| R | 3.5 | 1.2 | 1.56 | 2.7 | 0.99 | 1.2 | 2 | 0.97 |

R = A.I. SPA-S-843/A.I. Amphotericin B.

TABLE 5

In vitro therapeutic index (T.I.) of SPA-S-843 and of amphotericin B.
(T.I. = IC10 cells/IC 90 yeasts)

| | THERAPEUTIC INDEX | | |
|---|---|---|---|
| | L12010 | SR 4987 | BMC |
| SPA-S-843 | 22.43 | 15.89 | 3.5 |
| Amphotericin B | 8.42 | 13.37 | 2.28 |

TABLE 6

Prevention of experimental contamination.

| | | YEAST GROWTH (CFU/culture) | | | |
|---|---|---|---|---|---|
| | Pretreatment | Time after inoculum | | | |
| Cell line | (1 μg/ml) | 12 h | 24 h | 48 h | 72 h |
| L1210 | Untreated | 93 + 5 | 90 + 3 | 91 + 4 | 85 + 5 |
| L1210 | SPA-S-843 | 0 | 0 | 0 | 0 |
| L1210 | Amphotericin B | 58 + 6 | 4 + 2 | 3 + 1 | 12 + 4 |
| SR-4987 | Untreated | 91 + 3 | 85 + 5 | 83 + 5 | 90 + 3 |
| SR-4987 | SPA-S-843 | 0 | 0 | 0 | 0 |
| SR-4987 | Amphotericin B | 64 + 3 | 3 + 2 | 0 | 0 |

*C. albicans* inoculum = 100 CFU/culture
0: (Zero) = no colony detected under microscope

I claim:

1. A method for preventing and/or treating contamination of a cell or tissue culture in vitro or ex-vivo by a fungal agent, comprising adding to said cell culture or tissue an effective amount of a compound selected from the group consisting of derivatives of partricin A and derivatives of partricin B, wherein said cell or tissue culture comprises eukaryotic cells.

2. The method of claim 1, wherein said compound is selected from the group consisting of esters of the carboxyl group at C-18 of the macrolide ring of partricin A, amides of the carboxyl group at C-18 of the macrolide ring of partricin A, esters of the carboxyl group at C-18 of the macrolide ring of partricin B, amides of the carboxyl group at C-18 of the macrolide ring of partricin B, and pharmacologically and pharmaceutically acceptable organic and inorganic acids salts thereof.

3. The method of claim 1, wherein said compound is selected from the group consisting of derivatives of partricin A wherein the amino group of the mycosamine radical is substituted with an acyl group, derivatives of partricin B wherein the amino group of the mycosamine radical is substituted with an acyl group, and pharmacologically and pharmaceutically acceptable organic and inorganic acids salts thereof.

4. The method of claim 1, wherein said compound is selected from the group consisting of esters of the carboxyl group at C-18 of the macrolide ring of partricin A wherein the amino group of the mycosamine radical is substituted with an acyl group, amides of the carboxyl group at C-18 of the macrolide ring of partricin A wherein the amino group of the mycosamine radical is substituted with an acyl group, esters of the carboxyl group at C-18 of the macrolide ring of partricin B wherein the amino group of the mycosamine radical is substituted with an acyl group, amides of the carboxyl group at C-18 of the macrolide ring of partricin B wherein the amino group of the mycosamine radical is substituted with an acyl group, and pharmacologically and pharmaceutically acceptable organic and inorganic acids salts thereof.

5. The method of claim 1, wherein said compound is selected from the group consisting of secondary or tertiary amides on the carboxyl group at C-18 of the macrolide ring of partricin A, secondary or tertiary amides on the carboxyl group at C-18 of the macrolide ring of partricin B, and pharmacologically and pharmaceutically acceptable organic and inorganic acids salts thereof.

6. The method of claim 1, wherein said compound is selected from the group consisting of $C_1$–$C_6$ alkyl esters of the carboxyl group at C-18 of the macrolide ring of partricin A, $C_1$–$C_6$ alkyl esters of the carboxyl group at C-18 of the macrolide ring of partricin B, and pharmacologically and pharmaceutically acceptable organic and inorganic acids salts thereof.

7. The method of claim 1, wherein said compound is selected from the group consisting of partricin A in which the carboxyl group at C-18 of the macrolide ring is esterified with a $C_1$–$C_6$ alkyl group which contains a basic nitrogen substituent, partricin B in which the carboxyl group at C-18 of the macrolide ring is esterified with a $C_1$–$C_6$ alkyl group which contains a basic nitrogen substituent, and pharmacologically and pharmaceutically acceptable organic and inorganic acids salts thereof.

8. The method of claim 1, wherein said compound is selected from the group consisting of partricin A in which the carboxyl group at C-18 of the macrolide ring is bonded to an amide nitrogen which is bonded to a $C_1$–$C_6$ alkyl group and said $C_1$–$C_6$ alkyl group contains a basic nitrogen substituent, partricin B in which the carboxyl group at C-18 of the macrolide ring is bonded to an amide nitrogen which is bonded to a $C_1$–$C_6$, alkyl group and said $C_1$–$C_6$ alkyl group contains a basic nitrogen substituent, and pharmacologically and pharmaceutically acceptable organic and inorganic acids salts thereof.

9. The method of claim 1, wherein said compound is selected from the group consisting of derivatives of partricin A wherein the primary amino group of the mycosamine portion forms an amide bond with the carboxyl group of an aliphatic acid of 2–4 carbon atoms containing an additional basic nitrogen containing group, derivatives of partricin B wherein the primary amino group of the mycosamine portion forms an amide bond with the carboxyl group of an aliphatic acid of 2–4 carbon atoms containing an additional basic nitrogen containing group, and pharmacologically and pharmaceutically acceptable organic and inorganic acids salts thereof.

10. The method of claim 1, wherein said compound is selected from the group consisting of alkyl esters of the carboxyl group at C-18 of the macrolide ring of partricin A, alkyl esters of the carboxyl group at C-18 of the macrolide ring of partricin B, and pharmacologically and pharmaceutically acceptable organic and inorganic acids salts thereof.

11. The method of claim 1, wherein said compound is selected from the group consisting of $C_1$–$C_4$ alkyl esters of the carboxyl group at C-18 of the macrolide ring of partricin A, $C_1$–$C_4$ alkyl esters of the carboxyl group at C-18 of the macrolide ring of partricin B, and pharmacologically and pharmaceutically acceptable organic and inorganic acids salts thereof.

12. The method of claim 1, wherein said compound is selected from the group consisting of methyl esters of the carboxyl group at C-18 of the macrolide ring of partricin A, methyl esters of the carboxyl group at C-18 of the macrolide ring of partricin B, and pharmacologically and pharmaceutically acceptable organic and inorganic acids salts thereof.

13. The method of claim 1, wherein said compound is a water-soluble salt.

14. The method of claim 1, wherein said compound is N-dimethylaminoacetylpartricin A 2-dimethylaminoethylamide or its diascorbate.

15. The method of claim 1, wherein said compound has the all trans spatial configuration.

16. The method of claim 1, wherein said method is carried out in the prophylactic and/or curative form.

17. The method of claim 1, wherein said fungal agent is selected from the group consisting of yeasts and moulds.

18. The method of claim 1, wherein said cell culture comprises cells selected from the group consisting of animal cells, vegetable cells, and hybridomas.

19. The method of claim 1, wherein said cell culture comprises animal cells.

20. The method of claim 1, wherein said cell culture comprises human cells.

21. The method of claim 1, wherein said cell culture comprises cells obtained from a tissue.

22. The method of claim 1, wherein said cell culture comprises tumor cells.

23. The method of claim 1, wherein said cell culture comprises cells intended for the preparation of vaccines for human and veterinarian use.

24. The method of claim 1, wherein said cell culture comprises staminal cells.

25. The method of claim 1, wherein said cell culture comprises genetically modified cells.

26. The method of claim 1, wherein said tissues is any tissue or organ intended for transplantation.

* * * * *